US012729184B2

(12) United States Patent
Palle et al.

(10) Patent No.: US 12,729,184 B2
(45) Date of Patent: Sep. 8, 2026

(54) PROCESS FOR THE PREPARATION OF OLAPARIB, AND CRYSTALLINE FORM THEREOF

(71) Applicant: Alivus Life Sciences Limited, Solapur (IN)

(72) Inventors: Venkata Raghavendra Charyulu Palle, Pune (IN); Pratik R. Patel, Vadodara (IN); Nasir Ali, Thane (IN); Shivaji Haribhau Shelke, Thane (IN); Sachin Mahadeo Lad, Thane (IN); Girish Tilakchand Patle, Kalamboli-Panvel (IN); Raj Mahendra Shanmughasamy, Hosur (IN); Premkumar Ramraj Yadav, New Panvel (IN)

(73) Assignee: Alivus Life Sciences Limited, Solapur (IN)

( * ) Notice: Subject to any disclaimer, the term of this patent is extended or adjusted under 35 U.S.C. 154(b) by 360 days.

(21) Appl. No.: 18/682,361

(22) PCT Filed: Aug. 8, 2022

(86) PCT No.: PCT/IB2022/057356
§ 371 (c)(1),
(2) Date: Feb. 8, 2024

(87) PCT Pub. No.: WO2023/017393
PCT Pub. Date: Feb. 16, 2023

(65) Prior Publication Data

US 2024/0351989 A1 Oct. 24, 2024

(30) Foreign Application Priority Data

Aug. 9, 2021 (IN) ............................ 202121035948
Mar. 7, 2022 (IN) ............................ 202221012208

(51) Int. Cl.
*C07D 237/32* (2006.01)

(52) U.S. Cl.
CPC .................................. *C07D 237/32* (2013.01)

(58) Field of Classification Search
CPC .................................................... C07D 237/32
See application file for complete search history.

(56) References Cited

FOREIGN PATENT DOCUMENTS

| | | | | |
|---|---|---|---|---|
| CN | 105085407 A | * 11/2015 | ............ C07D 37/32 |
| CN | 110790710 A | 2/2020 | |
| WO | 2017123156 A1 | 7/2017 | |
| WO | WO-2018038680 A1 | * 3/2018 | ............ C07D 37/32 |
| WO | 2020256636 A1 | 12/2020 | |

OTHER PUBLICATIONS

Eric Valeur et al., "Amide bond formation: beyond the myth of coupling reagents," Chemical Society Reviews, 2009, pp. 606-631, 38.

* cited by examiner

*Primary Examiner* — Kamal A Saeed
*Assistant Examiner* — Sagar Patel
(74) *Attorney, Agent, or Firm* — Michael E. Carmen

(57) ABSTRACT

The present invention relates to a process for the preparation of olaparib. The present invention also relates to a novel crystalline form of olaparib, and a process for its preparation. Further, the present invention also relates to a pharmaceutical composition containing a therapeutically effective amount of the novel crystalline form of olaparib. Also, the present invention relates to improved processes for the preparation of crystalline form H and crystalline form A of olaparib.

17 Claims, 2 Drawing Sheets

Glenmark Life Sciences Limited
Figure 1/3
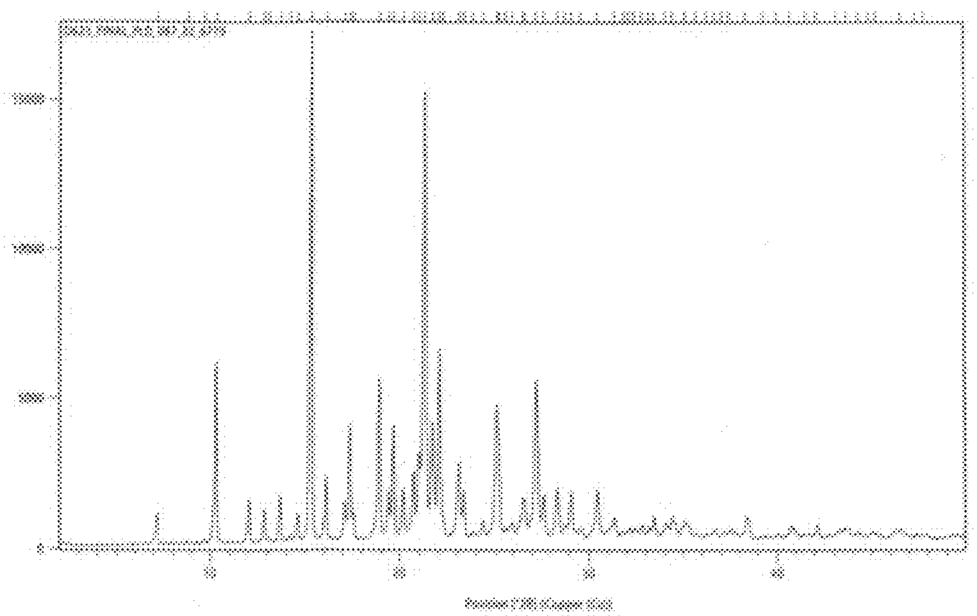
Glenmark Life Sciences Limited
Figure 2/3
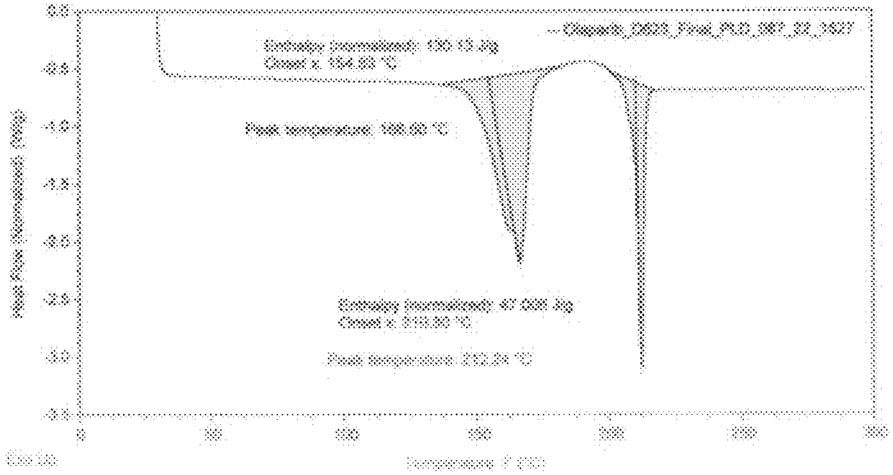

Glenmark Life Sciences Limited Figure 3/3
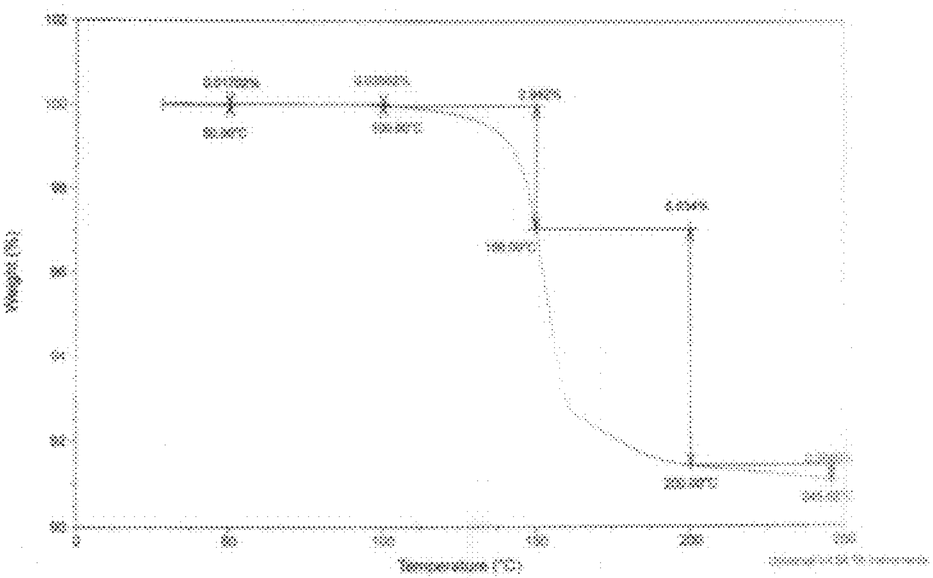

PROCESS FOR THE PREPARATION OF OLAPARIB, AND CRYSTALLINE FORM THEREOF

PRIORITY

This application claims priority under 35 U.S.C. § 371 to International Application No. PCT/IB2022/057356, filed Aug. 8, 2022, which claims the benefit of Indian Provisional Application No. 202121035948, entitled "Process for preparation of olaparib," filed Aug. 9, 2021, and Indian Provisional Application No. 202221012208, entitled "Crystalline form of olaparib and a process for its preparation," filed Mar. 7, 2022, the contents of each of which are incorporated herein by reference.

BACKGROUND OF THE INVENTION

Technical Field

The present invention relates to a process for the preparation of olaparib. The present invention also relates to a novel crystalline form of olaparib, and a process for its preparation. Further, the present invention relates to a pharmaceutical composition containing a therapeutically effective amount of the novel crystalline form of Olaparib. Also, the present invention relates to improved processes for the preparation of crystalline form H and crystalline form A of Olaparib.

Description of the Related Art

Olaparib, also known as, 4-[(3-{[4(cyclopropylcarbonyl) piperazin-1-yl]carbonyl}-4-fluorophenyl)methyl]phthalazin-1(2H)-one, is represented by the structure of formula I.

I

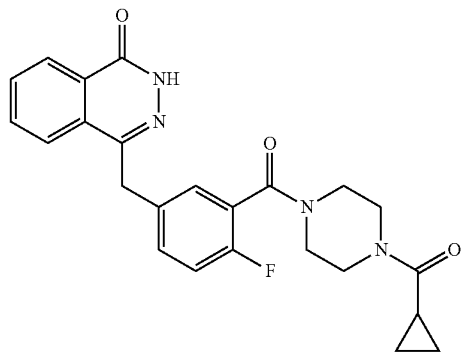

Olaparib is described in a published PCT application no. WO 2004/080976A1.

Olaparib is indicated for the treatment of ovarian cancer, breast cancer, pancreatic cancer, and prostate cancer.

SUMMARY OF THE INVENTION

The present invention provides a process for the preparation of olaparib, a compound of formula I (the "compound I"),

I

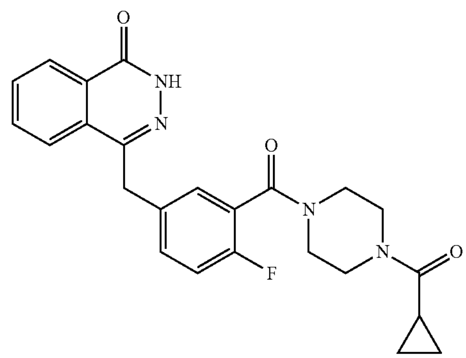

the process comprising:

(a) reacting 2-fluoro-5-formylbenzoic acid, a compound of formula V (the "compound V") with cyclopropyl (piperazin-1-yl) methanone, a compound of formula VI (the "compound VI") in the presence of a coupling agent,

V

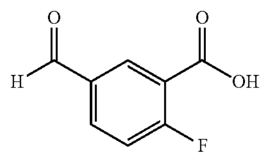

VI

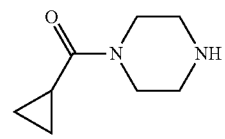

to obtain 3-{[4-(cyclopropylcarbonyl)piperazin-1-yl]carbonyl}-4-fluorobenzaldehyde, a compound of formula III (the "compound III"),

III

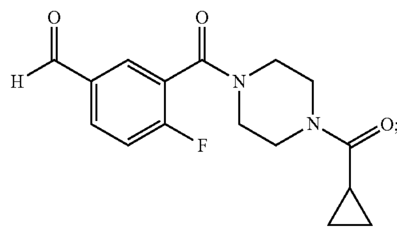

(b) reacting the compound III with dimethyl (3-oxo-1,3-dihydro-2-benzofuran-1-yl) phosphonate, a compound of formula IV (the "compound IV"),

IV

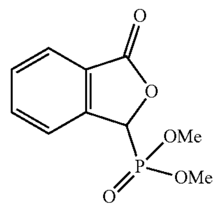

to obtain (3E/Z)-3-({3-[4-(cyclopropanecarbonyl)piperazine-1-carbonyl]-4-fluorophenyl]}methylidene)-2-benzofuran-1(3H)-one, a compound of formula II (the "compound II"),

II

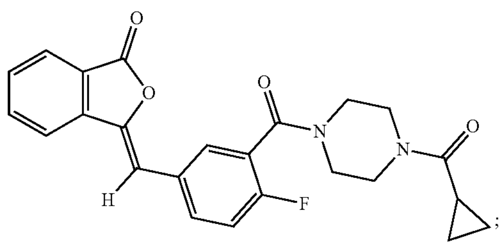

and (c) reacting the compound II with hydrazine hydrate to obtain olaparib, the compound I; wherein the compound III obtained in step (a) is not isolated.

The present invention also provides a crystalline form G1 of olaparib characterized by an X-ray powder diffraction (XRPD) spectrum having peak reflections at about 15.5, 21.5, 27.4, 30.6 and 38.4±0.2 degrees 2 theta.

The present invention also relates to a crystalline form G1 of Olaparib characterized by DSC thermogram having an endothermic peak at about 166.6° C. and 212.2° C.±2° C.

The present invention also provides an efficient process for the preparation of crystalline Form G1 of olaparib starting from (3E/Z)-3-({3-[4-(cyclopropanecarbonyl)piperazine-1-carbonyl]-4-fluorophenyl}methylidene)-2-benzofuran-1(3H)-one represented by the following formula II (the "compound II"),

II

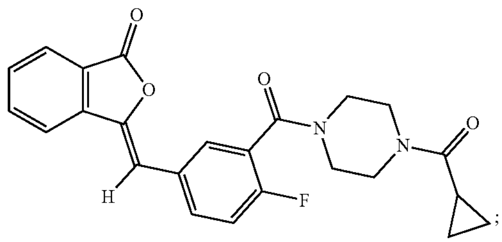

which reduces the formation of dimer impurity of olaparib (as described herein), and also, achieves crystallization and isolation of the desired crystalline form G1 of olaparib from reaction mass from the same pot.

The present invention also provides a process for the preparation of crystalline form G1 of olaparib, the process comprising:

(i) reacting a solution of compound II in a haloalkane solvent with hydrazine hydrate at a temperature ranging from about 20° C. to about 30° C. to obtain a reaction mixture;

(ii) stirring the reaction mixture as obtained in step (i) for about 8 hr to about 12 hr at a temperature ranging from about 20° C. to about 30° C. to obtain a reaction mass containing an intermediate compound represented by the following formula IIIa (the "compound IIIa") along with olaparib (the compound I);

IIIa

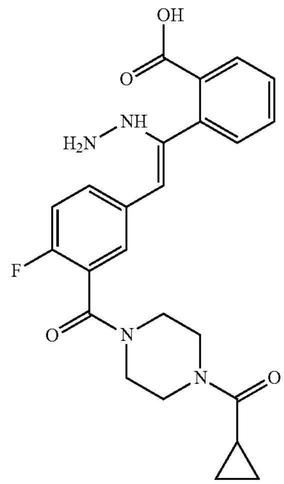

(iii) adding water to the reaction mass as obtained in the above step (ii), followed by stirring the mixture for about 10 minutes to 15 minutes to form layers from which the organic layer is separated;

(iv) adding an amide solvent to the organic layer as obtained in the above step (iii) followed by heating it to about 70° C. to obtain the compound I;

(v) adding haloalkane solvent to the reaction mass of step (iv), followed by stirring for about 2 hr to 4 hr at a temperature from about 20° C. to about 30° C.;

(vi) cooling the reaction mass as obtained in the above step (v) to a temperature ranging from about 10° C. to about 0° C. with stirring to obtain crystalline form G1 of olaparib; and (vii) isolating crystalline Form G1 of olaparib as obtained in step (vi).

The present invention also provides a process for the preparation of crystalline form G1 of Olaparib, the process comprising:

a) reacting a solution of compound II in an amide solvent with hydrazine hydrate at a temperature ranging from about 15° C. to about 35° C. to obtain a reaction mixture;

b) heating the reaction mixture as obtained in step (a) for about 3 hr to about 7 hr at a temperature ranging from about 60° C. to about 80° C. under stirring to obtain olaparib through compound IIIa;

c) adding a haloalkane solvent to the reaction mass as obtained in the above step (b) to obtain a clear solution, followed by stirring for about 1 hr to 3 hr at a temperature ranging from about 15° C. to about 35° C.;

d) cooling the reaction mass as obtained in the above step (c) to a temperature ranging from about 10° C. to about 0° C. with stirring to obtain crystalline form G1 of olaparib; and e) isolating crystalline Form G1 of olaparib as obtained in step (d).

The present invention also provides an improved process for the preparation of crystalline form H of olaparib as described herein.

The present invention also provides an improved process for the preparation of crystalline form A of olaparib as described herein.

BRIEF DESCRIPTION OF THE DRAWINGS

FIG. 1 is a characteristic X-ray Powder Diffraction Pattern (XRPD) of crystalline form G1 of Olaparib as obtained in Example 11.

FIG. 2 is a Differential Scanning Calorimetry (DSC) thermogram of crystalline form G1 of Olaparib as obtained in Example 11.

FIG. 3 is a Thermogravimetric analysis (TGA) of crystalline form G1 of Olaparib as obtained in Example 11.

DETAILED DESCRIPTION OF THE INVENTION

In one embodiment, the present invention provides a process for the preparation of olaparib, a compound of formula I (the "compound I"),

I

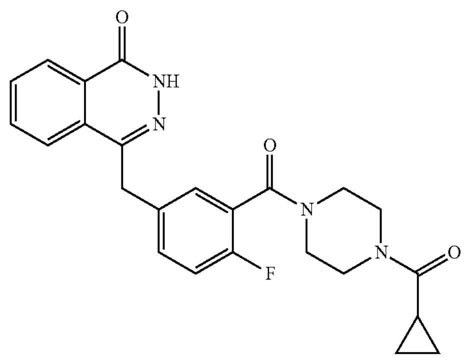

the process comprising:

(a) reacting 2-fluoro-5-formylbenzoic acid, a compound of formula V (the "compound V") with cyclopropyl (piperazin-1-yl) methanone, a compound of formula VI (the "compound VI") in the presence of a coupling agent,

V

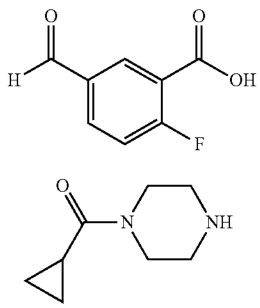

VI to obtain 3-{[4-(cyclopropylcarbonyl)piperazin-1-yl]carbonyl}-4-fluorobenzaldehyde, a compound of formula III (the "compound III"),

III

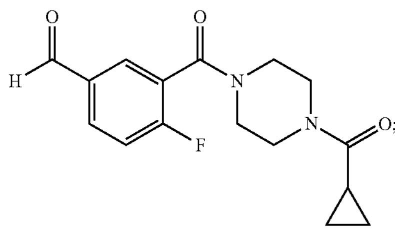

(b) reacting the compound III with dimethyl 3-oxo-1,3-dihydro-2-benzofuran-1-yl) phosphonate, a compound of formula IV (the "compound IV"),

IV

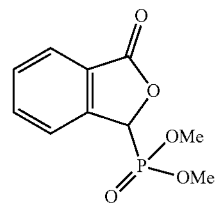

to obtain (3E/Z)-3-({3-[4-(cyclopropanecarbonyl)piperazine-1-carbonyl]-4-fluorophenyl}methylidene)-2-benzofuran-1(3H)-one, a compound of formula II (the "compound II"),

II

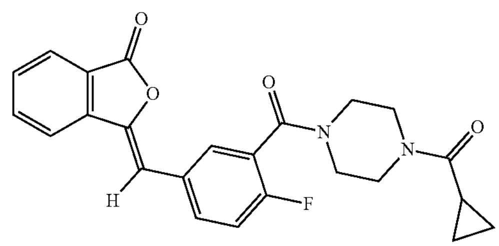

and (c) reacting the compound II with hydrazine hydrate to obtain olaparib, the compound I; wherein the compound III obtained in step (a) is not isolated.

In the context of the present invention, the term "room temperature" means a temperature of about 25° C. to about 30° C.

In one embodiment, as used herein, the term "about" refers to any value which lies within the range defined by a number up to 10% of the value.

In one embodiment, in step (a) of the process for the preparation of olaparib, the compound V is reacted with the compound VI in the presence of a coupling agent to obtain the compound III.

In one embodiment, the coupling agent is selected from the group consisting of EDCI (N-(3-dimethylaminopropyl)-N'-ethylcarbodiimide hydrochloride), DCC (dicyclohexylcarbodiimide), DIC (diisopropylcarbodiimide), HOBt (hydroxybenzotriazole hydrate), HOSu (N-hydroxysuccinimide), HOAt (1-hydroxy-7-azabenzotriazole), DEPBT (3-(diethoxyphosphoryloxy)-1,2,3-benzotriazin-4 (3H)-one), HOOBt (hydroxy-3,4-dihydro-4-oxo-1,2,3-benzotriazine), HBTU (N,N,N',N'-tetramethyl-O-(1H- benzotriazol-1-yl) uronium hexafluorophosphate), HDMC (N-[(5-Chloro-3-oxido-1H-benzotriazol-1-yl)-4-morpholinylmethylene]-N-methylmethanaminium hexafluorophosphate), HCTU (2-(6-chloro-1H-benzotriazole-1-yl)-1,1,3,3-tetramethylaminium hexafluorophosphate), HOTT (S-(1-oxido-2-pyridyl)-N,N,N',N'-tetramethylthiuronium hexafluorophosphate), TFFH (tetramethylfluoroformamidinium hexafluorophosphate), TBTU (O-(benzotriazol-1-yl)-N,N,N',N'-tetramethyluronium tetrafluoroborate), TATU (O-(7-azabenzotriazole-1-yl)-1,1,3,3-tetramethyluronium tetrafluoroborate), DMTMM (4-(4,6-dimethoxy-1,3,5-triazin-2-yl)-4-methylmorpholinium tetrafluoroborate), TSTU (N,N,N,N-tetramethyl-O—(N-succinimidyl)uronium tetrafluoroborate), TDBTU (O-(3,4-dihydro-4-oxo-1,2,3-benzotriazin-3-yl)-N,N,N',N'-tetramethyluronium tetrafluoroborate), TPTU (O-(2-oxo-1 (2H)pyridyl)-N,N,N',N'-tetramethyluronium tetrafluoroborate), TOTU (O-[(ethoxycarbonyl)cyanomethylenamino]-N,N,N',N'-tetramethyluronium tetrafluoroborate), TOTT (N,N,N',N'-tetramethyl-S-(1-oxido-2-pyridyl)thiouronium tetrafluoroborate), IIDQ (isobutyl 1,2-dihydro-2-isobutoxy-1-quinolinecarboxylate), EEDQ (N-Ethoxycarbonyl-2-ethoxy-1,2-dihydroquinoline), PyClU (chlorodipyrrolidinocarbenium hexafluorophosphate), PyOxim ([ethyl cyano (hydroxyimino)acetato-O2]tri-1-pyrrolidinylphosphonium hexafluorophosphate), PyAOP ((7-azabenzotriazol-1-yloxy) tripyrrolidinophosphonium hexafluorophosphate), PyBOP ((benzotriazol-1-yloxy)tripyrrolidinophosphonium hexafluorophosphate), BOP (benzotriazol-1-yloxytris(dimethylamino)phosphonium hexafluorophosphate), COMU ((1-cyano-2-ethoxy-2-oxoethylidenaminooxy)dimethyl-amino-morpholino-carbenium hexafluorophosphate), Oxyma (ethyl (hydroxyimino) cyanoacetate), FDPP (pentafluorophenyl diphenylphosphinate), T3P (propylphosphonic anhydride), TsCl (p-toluenesulfonyl chloride), and mixtures thereof.

In one embodiment, the reaction of the compound V with the compound VI occurs in the presence of a coupling agent, wherein the coupling agent is selected from EDCI, HOBt, or mixtures thereof.

In one embodiment, the reaction of the compound V with the compound VI occurs in the presence of a base.

In one embodiment, the base is selected from an organic base or an inorganic base.

The organic base includes, but is not limited to, diisopropylethylamine, triethylamine, tributylamine, triphenylamine, pyridine, lutidine (2,6-dimethylpyridine), collidine (2,4,6-trimethylpyridine), imidazole, DMAP (4-(dimethylamino) pyridine), DABCO (1,4-diazabicyclo[2.2.2]octane), DBU (1,8-diazabicyclo[5.4.0]undec-7-ene), DBN (1,5-diazabicyclo[4.3.0]non-5-ene), N,N,N',N'-tetramethyl-1,8-naphthalenediamine, oxyma (ethyl cyanohydroxyiminoacetate), HOBt (hydroxy benzotriazole hydrate), or mixtures thereof.

The inorganic base includes, but is not limited to, lithium carbonate, sodium carbonate, potassium carbonate, sodium bicarbonate, potassium bicarbonate, sodium hydroxide, potassium hydroxide, or mixtures thereof.

In one embodiment, the reaction of the compound V with the compound VI occurs in the presence of a base, wherein the base is selected from DMAP or HOBt.

In one embodiment, the reaction of the compound V with the compound VI occurs in the presence of a solvent.

In one embodiment, the solvent is selected from the group consisting of halogenated hydrocarbons, ethers, hydrocarbons, esters, nitriles, amides, sulfoxides, and mixtures thereof.

In one embodiment, the solvent is selected from the group consisting of halogenated hydrocarbons such as dichloromethane, dichloroethane, chloroform, and the like; ethers such as dimethyl ether, diethyl ether, diisopropyl ether, tert-butyl methyl ether, dibutyl ether, dimethoxyethane, diethoxyethane, tetrahydrofuran, dioxane and the like; hydrocarbons such as toluene, xylene, chlorobenzene, heptane, hexane, cyclohexane and the like; esters such as methyl acetate, ethyl acetate, n-propyl acetate, tert-butyl acetate and the like; nitriles such as acetonitrile, benzonitrile and the like; amides such as dimethylformamide, dimethyl acetamide and the like; sulfoxides such as dimethyl sulfoxide; and mixtures thereof.

In one embodiment, the reaction of the compound V with the compound VI occurs in the presence of a solvent, wherein the solvent is dichloromethane.

In one embodiment, the compound III obtained in step (a) is not isolated.

In the context of the present invention, the term "not isolated" means the intermediate referred to is not separated as a solid.

In one embodiment, the compound III obtained in step (a) is in-situ and carried forward to step (b).

In the context of the present invention, the term "in-situ" means the intermediate formed in the step referred to is not isolated.

In step (b) of the process for the preparation of olaparib, the compound III is reacted with the compound IV to obtain the compound II.

In one embodiment, the reaction of the compound III with the compound IV occurs in the presence of a base.

In one embodiment, the reaction of the compound III with the compound IV occurs in the presence of a base selected from the group consisting of diisopropylethylamine, trimethylamine, triethylamine, tributylamine, triphenylamine, pyridine, lutidine (2,6-dimethylpyridine), collidine (2,4,6-trimethylpyridine), imidazole, DMAP (4-(dimethylamino) pyridine), DABCO (1,4-diazabicyclo[2.2.2]octane), DBU (1,8-diazabicyclo[5.4.0]undec-7-ene), DBN (1,5-diazabicyclo[4.3.0]non-5-ene), N,N,N',N'-tetramethyl-1,8-naphthalenediamine, lithium hexamethyldisilazide, lithium carbonate, sodium carbonate, potassium carbonate, sodium bicarbonate, potassium bicarbonate, and mixtures thereof.

In one embodiment, the reaction of the compound III with the compound IV occurs in the presence of a base, wherein the base is selected from triethylamine, or diisoropylethylamine.

In one embodiment, the reaction of the compound III with the compound IV occurs in the presence of a solvent.

In one embodiment, the solvent is selected from the group consisting of ethers, halogenated hydrocarbons, hydrocarbons, esters, nitriles, amides, sulfoxides, and mixtures thereof.

In one embodiment, the solvent is selected from the group consisting of ethers such as dimethyl ether, diethyl ether, diisopropyl ether, tert-butyl methyl ether, dibutyl ether, dimethoxyethane, diethoxyethane, tetrahydrofuran, 2-methyltetrahydrofuran, dioxane and the like; halogenated hydrocarbons such as dichloromethane, dichloroethane, chloroform, and the like; hydrocarbons such as toluene, xylene, chlorobenzene, heptane, hexane, cyclohexane and the like; esters such as methyl acetate, ethyl acetate, n-propyl acetate, tert-butyl acetate and the like; nitriles such as acetonitrile, benzonitrile and the like; amides such as dimethylformamide, dimethyl acetamide and the like: sulfoxides such as dimethyl sulfoxide; and mixtures thereof.

In one embodiment, the reaction of the compound III with the compound IV occurs in the presence of a solvent, wherein the solvent is dichloromethane.

In one embodiment, in step (c) of the process for the preparation of olaparib, the compound II is reacted with hydrazine hydrate to obtain olaparib.

In one embodiment, the present invention provides a one-pot process for the preparation of the compound II, the process comprising:

(a) reacting the compound V, with the compound VI, in the presence of a coupling agent to obtain the compound III; and (b) reacting the compound III with dimethyl (3-oxo-1,3-dihydro-2-benzofuran-1-yl)phosphonate, the compound IV, to obtain the compound II.

In the context of the present invention, the term "one-pot" means the steps referred to, are in-situ and the intermediates are not isolated.

In one embodiment, the term "one-pot" means the process of the invention is carried out without isolation of the compound III in the form of a solid compound.

In one embodiment, the present invention provides a process for the preparation of olaparib, the compound I, from the compound II, wherein the compound II is prepared by a one-pot process comprising:

(a) reacting the compound V, with the compound VI, in the presence of a coupling agent to obtain the compound III; and (b) reacting the compound III with the compound IV, to obtain the compound II; and wherein the compound II obtained in step (b) is reacted with hydrazine hydrate to obtain olaparib, the compound I.

In one embodiment, the present invention provides a process for the preparation of olaparib, the compound I, the process comprising:

(a) reacting the compound V with the compound VI in the presence of a coupling agent is selected from the group consisting of EDCI, DCC, DIC, HOBt, HOSu, HOAt DEPBT, HOOBt, HBTU, HDMC, HCTU, HOTT, TFFH, TBTU, TATU, DMTMM, TSTU, TDBTU, TPTU, TOTU, TOTT, IIDQ, EEDQ, PyCIU, PyOxim, PyAOP, PyBOP, BOP, COMU, Oxyma, FDPP, T3P, TsCl, and mixtures thereof, to obtain compound III;

(b) reacting the compound III with the compound IV, to obtain compound II; and (c) reacting the compound II with hydrazine hydrate to obtain olaparib, the compound I.

In one embodiment, the present invention provides a process for the preparation of olaparib, the compound I, the process comprising:

(a) reacting the compound V with the compound VI in the presence of EDCI as the coupling agent to obtain the compound III;

(b) reacting the compound III with the compound IV, to obtain the compound II; and (c) reacting the compound II with hydrazine hydrate to obtain olaparib, the compound I.

In one embodiment, the present invention provides a process for the preparation of 2-fluoro-5-formylbenzoic acid, the compound V, the process comprising:

(a) reacting 2-fluoro-5-formylbenzonitrile, a compound of formula VIII (the "compound VIII"), with trimethyl orthoformate to obtain 5-(dimethoxymethyl)-2-fluorobenzonitrile, a compound of formula VII (the "compound VII"); and

VIII

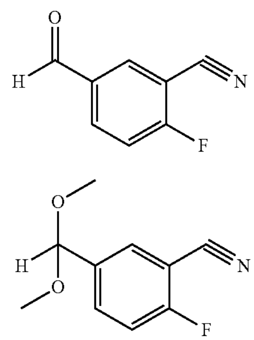

VII (b) hydrolyzing the compound VII, to obtain the compound V.

In one embodiment, in step (a) of the process for the preparation of the compound V, the compound VIII is reacted with trimethyl orthoformate to obtain 5-(dimethoxymethyl)-2-fluorobenzonitrile, the compound VII.

In one embodiment, step (a) of the process for the preparation of the compound V is performed in the presence of a solvent.

In one embodiment, the solvent is selected from the group consisting alcohols such as methanol, ethanol, n-propyl alcohol, isopropyl alcohol, n-butyl alcohol, isobutyl alcohol, sec-butyl alcohol, tert-butyl alcohol, pentanol, octanol and the like; halogenated hydrocarbons such as dichloromethane, chloroform, ethylene dichloride, and the like; dimethyl sulfoxide; dimethyl acetamide; water; and mixtures thereof.

In one embodiment, the compound VII may be isolated from the reaction mixture as an oily mass and then converted to the compound V.

In one embodiment, the compound VII obtained in step (a) is not isolated and carried forward for further reaction to obtain the compound V.

In one embodiment, in step (b) of the process for the preparation of the compound V, the compound VII is hydrolyzed to obtain the compound V.

In one embodiment, in step (b), the hydrolyzing agent is an acid or a base.

In one embodiment, the acid includes, but is not limited to, sulfuric acid, hydrochloric acid, hydrogen bromide, polyphosphoric acid, boron trifluoride, acetic acid and the like.

In one embodiment, the base includes, but are not limited to, sodium hydroxide, potassium hydroxide, lithium hydroxide, aqueous ammonia and the like.

In one embodiment, the reaction may be carried out at a temperature of about 40° C. to about 100° C. The stirring time may range from about 30 minutes to about 10 hours, or longer.

In one embodiment, the compound VII is hydrolyzed using base to obtain salt of 2-fluoro-5-formylbenzoic acid, the compound V.

In one embodiment, the compound VII is hydrolyzed using sodium hydroxide to obtain sodium salt of 2-fluoro-5-formylbenzoic acid, the compound V.

In one embodiment, sodium salt of 2-fluoro-5-formylbenzoic acid is treated with acid to obtain 2-fluoro-5-formylbenzoic acid, the compound V.

In one embodiment, sodium salt of 2-fluoro-5-formylbenzoic acid is treated with hydrochloric acid to obtain 2-fluoro-5-formylbenzoic acid, the compound V.

In one embodiment, the present invention provides a process for the preparation of 2-fluoro-5-formylbenzoic acid, the compound V, the process comprising hydrolyzing 2-fluoro-5-formylbenzonitrile, a compound VIII.

In one embodiment, the hydrolyzing agent is an acid or a base.

In one embodiment, the acid includes, but is not limited to, sulfuric acid, hydrochloric acid, hydrogen bromide, polyphosphoric acid, boron trifluoride.

In one embodiment, the base includes, but is not limited to, sodium hydroxide, potassium hydroxide, lithium hydroxide.

In one embodiment, the present invention provides an amorphous olaparib.

In one embodiment, the present invention provides a process for the preparation of amorphous form of olaparib comprising:

(a) providing a solution of olaparib in a solvent; and (b) isolating olaparib by:

(i) removing the solvent from the solution obtained in step (a); or (ii) combining the solution obtained in step (a) with an antisolvent followed by optional cooling; or (iii) slurring the compound obtained from step (b) (i); or (iv) cooling the solution obtained in step (a);

wherein the olaparib obtained is in amorphous form.

In one embodiment, providing a solution of olaparib in a solvent in step (a) comprises a solution obtained from reaction mixture in the final stage of process for preparation of olaparib.

In one embodiment, providing a solution of olaparib in a solvent in step (a) comprises a solution obtained after dissolving olaparib in a solvent.

In one embodiment, the solvent used in step (a) includes, but is not limited to, esters such as methyl acetate, ethyl acetate, propyl acetate, butyl acetate, tert-butyl acetate and the like; haloalkanes such as methylene dichloride, ethylene dichloride, chloroform and the like; acyclic ethers such as diethyl ether, dimethyl ether, ethyl methyl ether, diisopropyl ether, methyl tert-butyl ether, and the like; cyclic ethers such as tetrahydrofuran, dioxane, and the like; alcohols such as methanol, ethanol, 1-propanol, 2-propanol, 1-butanol, 2-butanol, 1-pentanol and the like; ketones such as acetone, ethyl methyl ketone, methyl isobutyl ketone and the like; aliphatic hydrocarbons such as hexane, heptane, cyclohexane and the like; aromatic hydrocarbons such as toluene, xylene, chlorobenzene and the like; nitriles such as acetonitrile, propanenitrile and the like; dimethyl sulfoxide; dimethyl formamide; dimethyl acetamide; water; or mixtures thereof.

In one embodiment, removal of the solvent in step (b)(i) may be carried out by solvent distillation, concentration, spray drying, fluid bed drying, lyophilization, flash drying, spin flash drying, or thin-film drying.

In one embodiment, removal of the solvent in step (b)(i) may be carried out by solvent distillation, preferably under vacuum.

In one embodiment, removal of the solvent in step (b)(i) may be carried out by spray drying.

In one embodiment, the anti-solvent used in step (b)(ii) is a solvent which on addition to a solution of olaparib in step (a) causes precipitation of olaparib owing to insolubility of olaparib in the solvent system generated.

In one embodiment, the anti-solvent used in step b(ii) may include esters, haloalkanes, alcohols, ketones, ethers, nitriles, hydrocarbons; water; or mixtures thereof.

In one embodiment, the antisolvent used in step b(ii) may be water.

In one embodiment, the antisolvent used in step b(ii) may be an aliphatic hydrocarbon such as n-hexane, n-heptane or cyclohexane.

In one embodiment, after the addition of the antisolvent as in step b(ii), optional cooling may be performed to obtain the precipitate.

In one embodiment, the present invention provides a process for preparation of amorphous form of olaparib comprising:

(a) providing a solution of olaparib in a solvent; and (b) isolating the amorphous form of olaparib by cooling the solution obtained in step (a) to a temperature of about −5° C. to 10° C.

In one embodiment, the amorphous form of olaparib obtained in step (b) may, optionally, be filtered and dried. Drying may be performed at a temperature of about 25° C. to about 110° C. Drying may be performed preferably in the presence of vacuum.

In one embodiment, the present invention provides a process wherein olaparib is obtained in a purity of ≥99.0%; and wherein the level of impurities designated herein as the impurity A, impurity B, impurity C, impurity D, impurity E or impurity F is less than 0.15% as determined by High Performance Liquid Chromatography (HPLC).

Impurity-A

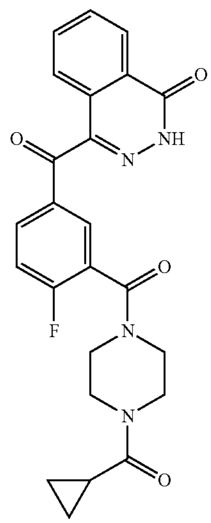

Impurity-B

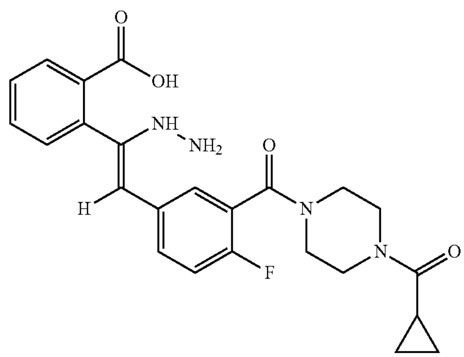

-continued

Impurity-C

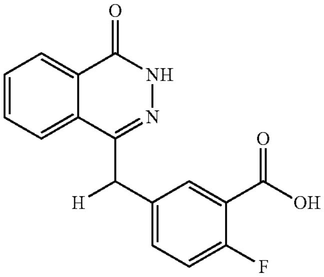

Impurity-D

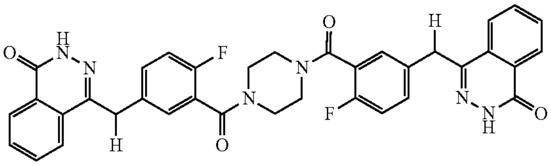

Impurity-E

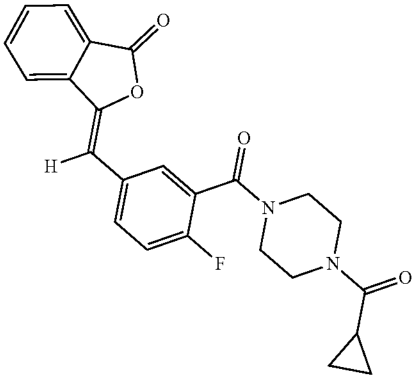

Impurity-F

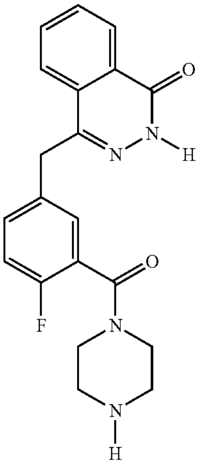

In one embodiment, olaparib, the compound I is obtained in a purity of ≥99.0% and wherein the level of any of the impurity as described above is less than 0.10%.

In one embodiment, olaparib, the compound I is obtained in a purity of ≥99.0% and wherein the level of any of the impurity as described above is less than 0.05%.

In one embodiment, olaparib, the compound I is obtained in a purity of ≥99.0% and wherein any of the impurity as described above is not detected.

In one embodiment, olaparib, the compound I is obtained in a purity of ≥99.5% and wherein the level of any of the impurity as described above is less than 0.15%.

The present invention also provides a novel crystalline form G1 of olaparib, which has been characterized by various techniques as described herein including, X-ray powder diffraction (XRPD) and differential scanning calorimetry (DSC).

In one embodiment, the present invention provides a crystalline form G1 of olaparib characterized by an X-ray powder diffraction (XRPD) spectrum having peak reflections at about 15.5, 21.5, 27.4, 30.6 and 38.4±0.2 degrees 2 theta.

In one embodiment, the present invention provides a crystalline form G1 of olaparib further characterized by an X-ray powder diffraction (XRPD) spectrum having peak reflections at about 19.4, 20.2 and 26.8±0.2 degrees 2 theta.

In one embodiment, the present invention provides a crystalline form G1 of olaparib characterized by an X-ray powder diffraction (XRPD) spectrum as illustrated or substantially illustrated in FIG. 1.

In one embodiment, the present invention provides a crystalline form G1 of Olaparib characterized by DSC thermogram having endothermic peaks at about 166.6° C. and 212.2° C.±2° C.

In one embodiment, the present invention provides a crystalline form G1 of Olaparib characterized by DSC thermogram as illustrated or substantially illustrated in FIG. 2.

In one embodiment, the present invention provides a crystalline form G1 of Olaparib characterized by an X-ray powder diffraction (XRPD) spectrum having peak reflections at about 15.5, 21.5, 27.4, 30.6 and 38.4±0.2 degrees 2 theta, and DSC thermogram having an endothermic peak at about 166.6° C. and 212.2° C.±2° C.

In one embodiment, the present invention provides a crystalline form G1 of Olaparib characterized by thermogravimetric analysis (TGA) thermogram as illustrated or substantially illustrated in FIG. 3, showing no weight loss up to 100° C.

In one embodiment, the present invention provides a crystalline form G1 of Olaparib characterized by an X-ray powder diffraction (XRPD) pattern as illustrated or substantially illustrated in FIG. 1, a DSC thermogram as illustrated or substantially illustrated in FIG. 2; a thermogravimetric analysis (TGA) as illustrated or substantially illustrated in FIG. 3, and any combination of the FIGS. 1, 2 and 3.

In the context of the present invention, the term "substantially illustrated" as used in reference to FIGS. 1, 2 and 3 may be understood to relate to any crystal form of olaparib characterized with the graphical data having small variations, as are well known to the person skilled in the art, in comparison with the FIG. 1, 2 or 3.

In one embodiment, the present invention provides an efficient process for the preparation of crystalline form G1 of olaparib, the compound I starting from (3E/Z)-3-({3-[4-(cyclopropanecarbonyl)piperazine-1-carbonyl]-4-fluorophenyl}methylidene)-2-benzofuran-1(3H)-one represented by the following formula II (the "compound II"),

II

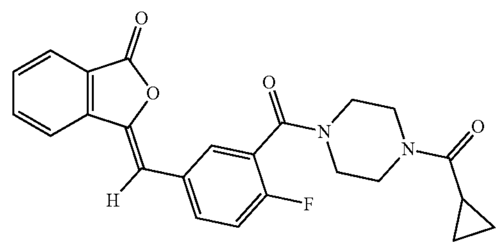

which reduces the formation of dimer impurity of olaparib (as described herein), and also, achieves crystallization and isolation of the desired crystalline form G1 of olaparib from reaction mass from the same pot.

In an embodiment, the present invention provides a process for the preparation of crystalline form G1 of olaparib, the process comprising:

(i) reacting a solution of compound II in a haloalkane solvent with hydrazine hydrate at a temperature ranging from about 20° C. to about 30° C. to obtain a reaction mixture;

(ii) stirring the reaction mixture as obtained in step (i) for about 8 hr to about 12 hr at a temperature ranging from about 20° C. to about 30° C. to obtain a reaction mass containing an intermediate compound represented by the following formula IIIa (the "compound IIIa") along with olaparib (the compound I);

IIIa

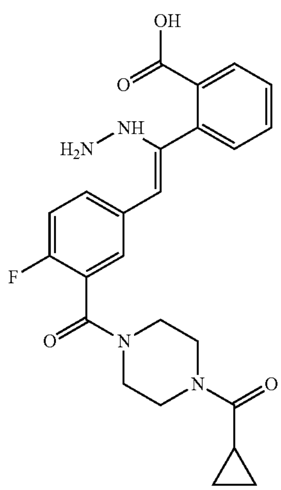

(iii) adding water to the reaction mass as obtained in the above step (ii), following by stirring the mixture for about 10 to 15 minutes to form layers from which the organic layer is separated;

(iv) adding an amide solvent to the organic layer as obtained in the above step (iii) followed by heating it to about 70° C. to obtain the compound I;

(v) adding haloalkane solvent to the reaction mass of step (iv), followed by stirring for about 2 to 4 hr at a temperature from about 20° C. to about 30° C.;

(vi) cooling the reaction mass as obtained in the above step (v) to a temperature ranging from about 10° C. to about 0° C. with stirring to obtain crystalline form G1 of olaparib; and (vii) isolating crystalline Form G1 of olaparib as obtained in step (vi).

In another embodiment, the present invention provides a process for the preparation of crystalline form G1 of olaparib, the process comprising:

a) reacting a solution of compound II in an amide solvent with hydrazine hydrate at a temperature ranging from about 15° C. to about 35° C. to obtain a reaction mixture;

b) heating the reaction mixture as obtained in step (a) for about 3 hr to about 7 hr at a temperature ranging from about 60° C. to about 80° C. under stirring to obtain Olaparib through compound IIIa;

c) adding a haloalkane solvent to the reaction mass as obtained in the above step (b) to obtain a clear solution, followed by stirring for about 1 hr to 3 hr at a temperature ranging from about 15° C. to about 35° C.;

d) cooling the reaction mass as obtained in the above step (c) to a temperature ranging from about 10° C. to about 0° C. with stirring to obtain crystalline form G1 of olaparib; and e) isolating crystalline Form G1 of olaparib as obtained in step (d).

In an embodiment, the present invention provides a process for the preparation of crystalline form G1 of olaparib, wherein the haloalkane solvent includes, but is not limited to, dichloromethane, chloroform, dichloroethane, and the like.

In an embodiment, the present invention provides a process for the preparation of crystalline form G1 of olaparib, wherein the amide solvent includes but is not limited to dimethylformamide, dimethylacetamide, and the like.

In one embodiment, the haloalkane solvent is dichloromethane.

In one embodiment, the amide solvent is dimethylacetamide.

In one embodiment, stirring in step (vi) and/or step (d) of the afore described processes of the present invention may be continued for any desired time period to obtain the desired crystalline form G1 of olaparib.

In an embodiment, stirring in step (vi) and/or step (d) of the afore described processes of the present invention may be done over a period ranging from about 2 hr to about 4 hr.

In an embodiment, in the process for the preparation of crystalline form G1 of olaparib, the crystalline form G1 of olaparib is isolated by any method known in the art. The method, may involve any of techniques, known in the art, including filtration by gravity or by suction, centrifugation, and the like.

In one embodiment, the isolated crystalline form G1 of olaparib may be further dried. Drying may be suitably carried out in an equipment conventionally used in the art for the purpose, such as a tray drier, a vacuum oven, an air oven, a fluidized bed drier, a spin flash drier, a flash drier and the like. The drying may be carried out at a temperature ranging from about room temperature to about 100° C. with or without vacuum. The drying may be carried out for any desired time until the required product quality is achieved. The drying time may vary from about 1 hr to about 25 hrs, or longer.

In one embodiment, the process(es) for the preparation of crystalline form G1 of olaparib as per the present invention provides olaparib substantially free of the known dimer impurity represented by the following chemical structure.

Dimer

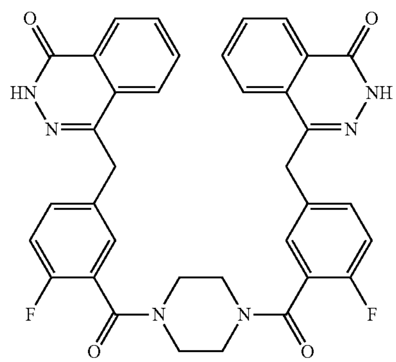

In one embodiment, the term "Olaparib substantially free of dimer impurity" as used herein means the amount of dimer impurity ranging from 0.05 to 0.10% by HPLC (High Performance Liquid Chromatography).

In one embodiment, the present invention also provides an improved process for the preparation of crystalline form H of Olaparib. Crystalline form H of olaparib is described in a published PCT application no. WO 2010/041051A1, having X-ray powder diffraction pattern containing specific peaks at 6.5, 6.9, 8.4 and 12.8±0.1 degrees 2 theta, and additional peaks at 15.1, 16.5, 16.8, 19.9 and 20.3±0.1 degrees 2 theta.

In an embodiment, the process for the preparation of crystalline form H of olaparib comprises:

(a) providing a solution of crystalline form G1 of olaparib in dimethylsulfoxide; and (b) obtaining crystalline form H of olaparib from the solution of step (a) by combining the solution of step (a) with water.

In one embodiment, step (a) may be carried out at a temperature from about 10° C. to about 60° C. Stirring may be continued for any desired time period to achieve a complete dissolution of olaparib. The solution may be optionally filtered to get a particle-free solution.

In the context of the present invention relating to the process for the preparation of crystalline form H of olaparib, the term "combining" means adding the solution of step (a) to water or adding water to the solution of step (a).

In one embodiment, step (b) may be carried out at a temperature from about 10° C. to about 60° C.

In one embodiment, step (b) may be carried out in the presence of form H seeds. In an embodiment, step (b) of the process may comprise use of water containing seed of pure form H of olaparib.

In an embodiment, the present invention relates to a process for the preparation of form H of olaparib starting from compound II, said process comprising:

(1) reacting a solution of compound II in dimethylsulfoxide with hydrazine hydrate at a temperature ranging from about 20° C. to about 30° C. to obtain a solution;

(2) heating the solution as obtained in step (1) for about 5 hr to about 9 hr at a temperature ranging from about 60° C. to about 70° C. under stirring to obtain a reaction mass;

(3) cooling the reaction mass as obtained in the above step (2) to a temperature ranging from about 20° C. to about 30° C., and filtering it to obtain a filtrate;

(4) adding the filtrate as obtained in step (3) to water, and the resulting reaction mass was stirred;

(5) isolating crystalline Form H of olaparib as obtained in step (4).

In one embodiment, stirring in step (2) of the process for the preparation of form H of olaparib starting from the compound II is done over a period ranging from about 6 hr to about 9 hr. In one embodiment, stirring in step (2) is done for 8 hr.

In one embodiment, the step (4) may be carried out in the presence of form H seeds. In an embodiment, the step (4) of the process may comprise use of water containing seed of pure form H of olaparib.

In one embodiment, stirring in the step (4) of the process for preparation of form H of olaparib starting from the compound II is done over a period ranging from about 9 hr to about 15 hr. In one embodiment, stirring in the step (4) is done for about 12 hr.

In one embodiment, stirring in the step (4) of the process for the preparation of form H of olaparib starting from compound II is done at a temperature ranging from about 20° C. to about 30° C.

In one embodiment, the crystalline form H of olaparib obtained as per the process of the present invention is substantially free of crystalline form A and/or crystalline form L of Olaparib.

In one embodiment, the term "substantially free" means the amount referred to is in no detectable quantity.

In the context of the present invention relating to the process for the preparation of crystalline form H of olaparib, the term "no detectable quantity" refers to crystalline form A and/or crystalline form L of olaparib in an amount of less than about 0.5% w/w. Preferably, less than about 0.1% w/w; still more preferably, absent.

In one embodiment, the crystalline form H of olaparib obtained in the step (b) is stable.

As used herein, the term "stable" refers to crystalline form H of olaparib which retains its original polymorphic form without undergoing polymorphic conversion over time.

In one embodiment, the stable crystalline form H of olaparib obtained by the process as described herein above has no detectable quantity of form A and/or form L of olaparib on storage.

In one embodiment, the stable form H of olaparib obtained by the process as described herein above has no detectable quantity of form A and/or form L of olaparib at room temperature or under accelerated stability conditions for extended periods of time.

In one embodiment, the present invention provides pharmaceutical compositions comprising the crystalline form G1 of olaparib obtained by the processes herein described.

In an embodiment, the present invention relates to a process for the preparation of Form A of olaparib starting from compound II, said process comprising:

(i) reacting a solution of compound II in dimethylacetamide with hydrazine hydrate at a temperature ranging from about 20° C. to about 30° C. to obtain a solution;

(ii) heating the solution as obtained in step (i) for about 3 hr to about 8 hr at a temperature ranging from about 60° C. to about 90° C. under stirring to obtain a reaction mass;

(iii) adding ethyl acetate solvent to the reaction mass as obtained in the above step (ii) at a temperature ranging from about 20° C. to about 40° C.;

(iv) stirring the reaction mass as obtained in the above step (iii) for about 4 hr to 7 hr at a temperature ranging from about 15° C. to about 35° C.;

(v) filtering the reaction mass as obtained in the above step (iv) to obtain a filtrate;

(vi) isolating crystalline Form A of olaparib as obtained in step (v).

In one embodiment, stirring in step (ii) of the process for the preparation of form A of olaparib starting from the compound II is done over a period ranging from about 3 hr to about 8 hr. In one embodiment, stirring in step (ii) is done for 4 hr.

In one embodiment, stirring in the step (iv) of the process for preparation of form A of olaparib starting from the compound II is done over a period ranging from about 4 hr to about 7 hr. In one embodiment, stirring in the step (iv) is done for about 6 hr.

In one embodiment, stirring in the step (iv) of the process for the preparation of form A of olaparib starting from compound II is done at a temperature ranging from about 15° C. to about 35° C.

In an embodiment, the process for the preparation of crystalline form A of Olaparib comprises:

(a) providing a solution of crystalline form G1 of olaparib in a water-miscible solvent and water;

(b) stirring the reaction mass obtained from solution of step (a) at a temperature from about 0° C. to about 10° C.;

(c) filtering the reaction mass obtained from solution of step (b); and (d) obtaining crystalline form A of olaparib from step (c) by combining the filtered reaction mass of step (c) with water.

In an embodiment, in the process for the preparation of crystalline form A of olaparib, in step (a), the water-miscible solvent includes, but is not limited to, methanol, ethanol, propanol, isopropanol, butanol, acetone, dimethylacetamide and the like.

In one embodiment, step (a) may be carried out at a temperature from about 65° C. to about 80° C.

In one embodiment, in step (b), the stirring may be carried out at a temperature from about 10° C. to about 60° C. Stirring may be continued for any desired time period to achieve a complete dissolution of olaparib.

In one embodiment, step (b) may be carried out in the presence of form A seeds. In an embodiment, step (b) of the process may comprise use of water containing seeds of pure form A of olaparib.

In the context of the present invention relating to the process for the preparation of crystalline form A of Olaparib, the term "combining" means adding the filtered reaction mass obtained in step (c) to water.

In one embodiment, the present invention provides pharmaceutical compositions comprising olaparib obtained by the processes herein described, having a $D_{90}$ particle size of less than about 250 microns, preferably less than about 150 microns, more preferably less than about 50 microns, still more preferably less than about 20 microns, still more preferably less than about 15 microns, and most preferably less than about 10 microns.

In one embodiment, the present invention provides pharmaceutical compositions comprising olaparib obtained by the processes herein described, having a $D_{50}$ particle size of less than about 250 microns, preferably less than about 150 microns, more preferably less than about 50 microns, still more preferably less than about 20 microns, still more preferably less than about 15 microns, and most preferably less than about 10 microns.

The particle size disclosed here can be obtained by, for example, any milling, grinding, micronizing or other particle size reduction method known in the art to bring the solid state olaparib into any of the foregoing desired particle size range.

The examples that follow are provided to enable one skilled in the art to practice the invention and are merely illustrative of the invention. The examples should not be read as limiting the scope of the invention as defined in the claims.

EXAMPLES

Example 1: Preparation of 5-(dimethoxymethyl)-2-fluorobenzonitrile (Compound VII)

To a suspension of 2-fluoro-5-formylbenzonitrile (10 g), ammonium chloride (0.14 g) and methanol (8 mL) cooled to about 0-5° C., was added trimethyl orthoformate (7.8 g) in about 25 min. The reaction mixture was warmed to about 20-30° C. and stirred for about 12 h. The reaction mixture was concentrated and degassed under vacuum at about 45° C. to obtain oily mass. Yield: 12.94 g (99%); HPLC purity: 95%

Example 2: Preparation of sodium 5-(dimethoxymethyl)-2-fluorobenzoate

Aqueous sodium hydroxide solution (3N, 44 mL) was added to an oily mass of 5-(dimethoxymethyl)-2-fluorobenzonitrile (12.94 g) and the reaction mixture was stirred at about 60-70° C. for about 10 h. The reaction mixture was concentrated under vacuum at about 50-60° C. to obtain white solid. Yield: 15.35 g (98%); HPLC purity: 97%

Example 3: Preparation of 2-fluoro-5-formylbenzoic acid (Compound V)

Water (44 mL) was added to sodium 5-(dimethoxymethyl)-2-fluorobenzoate (15.3 g) and the reaction mixture was stirred for about 5-10 min. The pH of the reaction mixture was adjusted to about 1.5-2.5 using 3N hydrochloric acid. The reaction mixture was stirred for about 3-4 h at about 20-30° C., filtered and washed with water. The solid obtained was dried in Air Tray Drier (ATD). Yield: 9.93 g (91%); HPLC Purity: 99%

Example 4: Preparation of 2-fluoro-5-formylbenzoic acid (Compound V)

To a mixture of 2-fluoro-5-formyl benzonitrile (Compound VIII, 10 g), ammonium chloride (0.14 g) and methanol (8.2 mL), was added trimethyl orthoformate (7.8 g) at about 0-5° C. The reaction mixture was slowly warmed to about 20-30° C. and stirred for about 14 h. The reaction mixture was concentrated and degassed under vacuum at about 45° C. to obtain oily mass. Aqueous sodium hydroxide solution (3N, 44 mL) was added to the oily mass and the reaction mixture was stirred at about 60-70° C. The reaction mixture was cooled to about 25° C. and the pH was adjusted to about 1.5-2.5 using 3N hydrochloric acid. The reaction mixture was stirred for about 3-4 h, filtered and washed with water. The solid obtained was dried in ATD at about 45-55° C. Yield: 10.36 g (92%); HPLC Purity: 99.4%

Example 5: Preparation of 3-{[4-(cyclopropylcarbonyl)piperazin-1-yl]carbonyl}-4-fluorobenzaldehyde (Compound III)

A solution of 2-fluoro-5-formylbenzoic acid (Compound V, 10 g) in methylene dichloride (40 mL) was cooled to about 0° C. to about −5° C. Cyclopropyl(piperazin-1-yl) methanone (Compound VI, 10 g) in methylene dichloride (10 mL) was added to the reaction mixture at about 0° C. to about −5° C. and stirred for about 5-10 min. 1-Hydroxy benzotriazole (0.8 g) and 1-(3-dimethylaminopropyl)-3-ethylcarbodiimide hydrochloride (13.6 g) was added simultaneously to the reaction mixture at about 0-5° C. and stirred for about 2-3 h. 5% aqueous sodium bicarbonate solution was added to the reaction mixture which was stirred for about 20-30 min at about 20-30° C. The two layers were separated and the organic layer was washed with water, concentrated and degassed under vacuum at about 40° C. to obtain a residue. Tert-butyl methyl ether was added to the residue and the mixture was stirred for about 3-4 h, filtered, washed with tert-butyl methyl ether. The solid obtained was dried in Vacuum Tray Drier (VTD) at about 45-50° C. Yield: 17.1 g (95%); HPLC Purity: 98%

Example 6: Preparation of (3E/Z)-3-({3-[4-(cyclopropanecarbonyl)piperazine-1-carbonyl]-4-fluorophenyl}methylidene)-2-benzofuran-1(3H)-one (Compound II)

To a mixture of 3-{[4-(cyclopropylcarbonyl)piperazin-1-yl]carbonyl}-4-fluoro benzaldehyde (Compound III, 10 g) and dimethyl (3-oxo-1,3-dihydro-2-benzofuran-1-yl) phosphonate (Compound IV, 8.09 g) in methylene dichloride (50 mL) cooled to about 0-10° C., was added diisopropylethylamine (4.4 g). The temperature was raised to about 20-30° C. and the reaction mixture was stirred for about 12 h. 1N hydrochloric acid was added to the reaction mixture which was stirred for about 10-20 min. The two layers were separated and the organic layer was washed with water, concentrated and degassed under vacuum at about 40° C. to obtain residue. Acetone was added to the residue and the mixture was concentrated and degassed under vacuum at about 40° C. to obtain semisolid residue. Acetone was added to the semisolid residue and the reaction mixture was stirred for about 45-60 min. Water was added to the reaction mixture at about 20-30° C. The reaction mixture was stirred for about 8-10 h at about 20-30° C., filtered and washed with water. The solid obtained was dried in ATD at about 45-50° C. Yield: 12.40 g (90%); HPLC Purity: 99.6%

Example 7: Preparation of (3E/Z)-3-({3-[4-(cyclopropanecarbonyl)piperazine-1-carbonyl]-4-fluorophenyl}methylidene)-2-benzofuran-1(3H)-one (Compound II)

A solution of cyclopropyl(piperazin-1-yl) methanone (Compound VI, 10 g) in methylene dichloride (10 mL) was added to a solution of 2-fluoro-5-formyl benzoic acid (Compound V, 10 g) in methylene dichloride (40 mL) at about 0-5° C. and the reaction mixture was stirred for about 5-10 min. 1-Hydroxybenzotriazole (0.8 g) and EDCI (1-(3-dimethylaminopropyl)-3-ethylcarbodiimide hydrochloride) (13.6 g) was added simultaneously to the reaction mixture at about 0-5° C. and stirred for about 2-3 h. 5% aqueous sodium bicarbonate solution was added into the reaction mixture and stirred for about 20-30 min at about 20-30° C. The two layers were separated and the organic layer was washed with water and azeotropically partially distilled at about 40° C. To the concentrated methylene dichloride layer containing product was added methylene dichloride (20 mL) and the mixture was cooled to about 20-30° C. Dimethyl (3-oxo-1,3-dihydro-2-benzofuran-1-yl)phosphonate (Compound IV, 14.7 g) was added and the reaction mixture was cooled at about 0-10° C. Diisopropylethylamine (8.05 g) was added to the reaction mixture at about 0-10° C., the temperature was raised to about 20-30° C. and the reaction mixture was stirred for about 12 h. 1N hydrochloric acid was added to the reaction mixture at about 25° C. and stirred for about 10-20 min. The two layers were separated and the organic layer was washed with water, concentrated and degassed under vacuum at about 40° C. to obtain semisolid residue. Acetone was added to the semisolid residue and the reaction mixture was stirred for about 45-60 min. Water was added to the reaction mixture at about 20-30° C. The reaction mixture was stirred for about 3-4 h at about 20-30° C., filtered and washed with water. The solid obtained was dried in ATD at about 45-50° C. Yield: 22 g (88%); HPLC Purity: 99.5%

Example 8: Preparation of 3-{[4-(cyclopropylcarbonyl)piperazin-1-yl]carbonyl}-4-fluorobenzaldehyde (Compound III)

To a solution of 2-fluoro-5-formylbenzoic acid (Compound V, 10 g) in methylene dichloride (40 mL) was cooled to about 0° C. to about −5° C., was added cyclopropyl (piperazin-1-yl)methanone (Compound VI, 10 g) in methylene dichloride (10 mL) and the reaction mixture was stirred for about 5-10 min. 4-(N,N-dimethylamino)pyridine (0.36 g) and EDCI (1-(3-dimethylaminopropyl)-3-ethylcarbodiimide hydrochloride) (13.6 g) was added simultaneously to the reaction mixture at about 0° C. to about −5° C. and stirred for about 2-3 h. 5% aqueous sodium bicarbonate solution was added to the reaction mixture which was stirred for about 20-30 min at about 20-30° C. The two layers were separated and the organic layer was washed with water, concentrated and degassed under vacuum at about 35-40° C. to obtain residue. Tert-butyl methyl ether was added to the residue and the mixture was stirred for about 3-4 h, filtered, washed with tert-butyl methyl ether. The solid was dried in VTD at about 45-50° C. Yield: 13.6 g (75%); HPLC Purity: 95%

Example 9: Preparation of (3E/Z)-3-({3-[4-(cyclopropanecarbonyl) piperazine-1-carbonyl]-4-fluorophenyl}methylidene)-2-benzofuran-1(3H)-one (Compound II)

To a solution of 3-{[4-(cyclopropylcarbonyl)piperazin-1-yl]carbonyl}-4-fluoro benzaldehyde (Compound III, 10 g) and dimethyl (3-oxo-1,3-dihydro-2-benzofuran-1-yl) phosphate (Compound IV, 8.09 g) in methylene dichloride (40 mL) cooled to about 0-10° C., was added triethylamine (3.46 g). The temperature was raised to about 20-30° C. and the reaction mixture was stirred for about 12 h. 1N hydrochloric acid was added to the reaction mixture at about 25° C. and stirred for about 10-20 min. The two layers were separated and the organic layer was washed with water, concentrated and degassed under vacuum at about 40° C. to obtain residue. Acetone was added to the residue and the mixture was concentrated and degassed under vacuum at about 40° C. to obtain semisolid residue. Acetone was added to the semisolid residue and the reaction mixture was stirred for about 5-10 min. Water was added to the reaction mixture at about 20-30° C. The reaction mixture was stirred for about 3-4 h at about 20-30° C., filtered and washed with water. The solid obtained was dried in ATD at about 45-50° C. Yield: 9.70 g (70%); HPLC Purity: 99.35%

Example 10: Preparation of (3E/Z)-3-({3-[4-(cyclopropanecarbonyl)piperazine-1-carbonyl]-4-fluorophenyl}methylidene)-2-benzofuran-1(3H)-one (Compound II)

A solution of cyclopropyl(piperazin-1-yl) methanone (Compound VI, 10 g) in methylene dichloride (10 mL) was added to a solution of 2-fluoro-5-formylbenzoic acid (Compound V, 10 g) in methylene dichloride (40 mL) at about 0° C. to about −5° C. and the reaction mixture was stirred for about 5-10 min. 4-(N,N-dimethylamino)pyridine (0.36 g) and EDCI (1-(3-dimethylaminopropyl)-3-ethylcarbodiimide hydrochloride) (13.6 g) was added simultaneously to the reaction mixture at about 0° C. to about −5° C. and stirred for about 2-3 h. 5% aqueous sodium bicarbonate solution was added to the reaction mixture and stirred for about 20-30 min at about 20-30° C. The two layers were separated and the organic layer was washed with water and azeotropically partially distilled at about 40° C. Methylene dichloride (20 mL) was added to the concentrated methylene dichloride layer and cooled to about 20-30° C. Dimethyl-(3-oxo-1,3-dihydro-2-benzofuran-1-yl)phosphonate (Compound IV, 14.7 g) was added and the reaction mixture was cooled at about 0-10° C. Triethylamine (6.3 g) was added to the reaction mixture at about 0-10° C., the temperature was raised to about 20-30° C. and the reaction mixture was stirred for about 12 h. 1N hydrochloric acid was added to the reaction mixture which was stirred for about 10-20 min. The two layers were separated and the organic layer was washed with water, concentrated and degassed under vacuum at about 40° C. to obtain residue. Acetone was added to the residue and the mixture was concentrated and degassed under vacuum at about 40° C. to obtain semisolid residue. Acetone was added to the semisolid residue and the reaction mixture was stirred for about 45-60 min. Water was added to the reaction mixture at about 20-30° C. The reaction mixture was stirred for about 8-10 h at about 20-30° C., filtered and washed with water. The solid obtained was dried in ATD at about 45-50° C. Yield: 16.25 g (65%); HPLC Purity: 99.55%

Example 11: Preparation of Olaparib form G1

To a solution of (3E/Z)-3-({3-[4-(cyclopropanecarbonyl) piperazine-1-carbonyl]-4-fluorophenyl}methylidene)-2-benzofuran-1(3H)-one (Compound II, 5 g) in dimethyl acetamide (5 mL) added hydrazine hydrate (0.89 g) at a temperature of about 25° C. to about 35° C. The reaction mass was stirred at about 70° C. to about 80° C. for about 5 h. The completion of reaction was monitored by HPLC. After completion of reaction, dichloromethane was added to the reaction mass. The clear solution was obtained, stirred for about 2 h at about 25° C. to about 35° C. and cooled to about 5° C. to about 10° C. under stirring. The obtained solid was filtered under vacuum, washed with dichloromethane and dried under vacuum for about 45° C. to about 50° C. for about 12 h to obtain title product. Dry weight: 4 g, Yield: 80% w/w.

Example 12: Preparation of Olaparib Form H

Olaparib (5 g, as obtained from Example 1) was dissolved in dimethyl sulfoxide (30 mL) at a temperature of about 25° C. to about 30° C. and the resulting solution was filtered through hyflow bed. The filtrate was slowly added under stirring to the purified water (100 mL) containing seed of pure Olaparib Form H (100 mg) at a temperature of about 25° C. to about 30° C. The reaction mass was stirred for about 12-14 h at the same temperature, filtered under vacuum, and washed with purified water. The obtained wet material was dried under vacuum at a temperature of about 40° C. to about 50° C. for about 12 h. Dry weight: 4 g. Yield: 80% w/w.

Example 13: Preparation of Olaparib Form G1

To a solution of (3E/Z)-3-({3-[4-(cyclopropanecarbonyl) piperazine-1-carbonyl]-4-fluorophenyl}methylidene)-2-benzofuran-1(3H)-one (Compound II, 5 g) in dichloromethane (50 mL) was added hydrazine hydrate (0.89 g) at a temperature of about 25° C. to about 30° C. and the obtained clear reaction mass was stirred for about 10-12 h.

The reaction was monitored by HPLC. The formation of intermediate (the compound IIIa) along with Olaparib was observed in HPLC. To the reaction mass, purified water (25 mL) was added, stirred for about 10 min and layers formed were separated.

The organic layer was distilled under vacuum at temperature of about below: 40° C. Dimethyl acetamide (15 mL) was added to the reaction mass and heated to about 70° C. After completion of reaction, dichloromethane was added to the reaction mass, stirred for about 3 h at a temperature of about 25° C. to about 30° C. and cooled to about 5-10° C. The obtained solid was filtered under vacuum, washed with dichloromethane. The wet material was dried under vacuum at about 45-50° C. for about 12 h. Dry weight: 3.5 g (Olaparib), Yield: 70% w/w.

Example 14: Direct Isolation of Olaparib Form-H

To a solution of (3E/Z)-3-({3-[4-(cyclopropanecarbonyl) piperazine-1-carbonyl]-4-fluorophenyl}methylidene)-2-benzofuran-1(3H)-one (compound II, 5 g) in dimethyl sulfoxide (30 mL) was added hydrazine hydrate (0.89 g) at a temperature of about 25° C. to about 30° C. and the obtained clear reaction mass was heated under stirring at about 65° C. to about 70° C. for about 8 h. The reaction mass was cooled at about 25° C. to about 30° C. and stirred for about 12-15 h. The obtained solid was filtered under vacuum and washed with purified water. The wet material was dried under vacuum at about 45° C. to about 50° C. for about 12 h. Dry weight: 4 g, Yield: 80% w/w.

Example 15: Preparation of Olaparib Form A

Olaparib form G1 (5 g, as obtained from Example 11) was mixed with ethanol (15 mL) and purified water (5 mL) and reaction mass was heated to about 70-75° C. to get clear solution. Clear solution was distilled under vacuum at below 70° C. Ethanol (26.25 mL) and purified water (5 mL) was added to the obtained residue and reaction mass was heated to about 70-75° C. to obtain clear solution. Clear solution was stirred for about 1 hr at about 70-75° C. and gradually cooled to about 30-35° C. Seeding of Form-A (100 mg) is added to the solution and solution was further cooled to about 0-10° C. The reaction mass was further stirred for about 8 hr at about 0-10° C. The reaction mass was filtered through Buchner funnel under vacuum, washed with mixture of ethanol and water (50:50). The obtained wet material was mixed with purified water, heated at about 70° C. and stirred for about 30 min at about 70° C. Reaction mass was cooled to about 20-25° C., stirred for about 30 min, filtered and dried in vacuum oven at about 60° C. for about 12 hr. Dry Weight: 4 g. Yield: 80% w/w. Particle size: D (0.1): 3.34, D (0.5): 28.73, D (0.9): 80.20

Example 16: Purification of Olaparib

Olaparib form G1 (5 g, as obtained from Example 11) was mixed with dimethyl acetamide (10 mL) and dichloromethane (40 mL). The slurry mass obtained was heated to about 50-60° C. under stirring. The reaction mass was stirred for about 1 hr at about 50-60° C., gradually cooled to about 20-25° C. and further cooled to 0-10° C. The reaction mass was stirred for about 8-10 hr, filtered and obtained wet material was dried in vacuum oven at about 50-55° C. for about 12 hr. Dry weight: 4 g. Yield: 80% w/w.

Example 17: Direct Isolation of Olaparib Form A

To a solution of (3E/Z)-3-({3-[4-(cyclopropanecarbonyl) piperazine-1-carbonyl]-4-fluorophenyl}methylidene)-2- benzofuran-1(3H)-one (Compound II, 30 g) in dimethyl acetamide (60 mL) was added hydrazine hydrate (4.9 g) at a temperature of about 25° C. to about 35° C. The reaction mass was stirred at about 70-80° C. for about 4 h. The completion of reaction was monitored by HPLC. After completion of reaction, ethyl acetate was added to the reaction mass at about 25-35° C. The reaction mass was stirred for about 6 hr at about 20-30° C. The obtained solid was filtered under vacuum, washed with ethyl acetate and dried under vacuum for about 50-60° C. for about 12 hr to obtain titled product. Dry weight: 26 g. Yield: 86% w/w.

The invention claimed is:

1. A process for the preparation of olaparib, a compound of formula I,

I

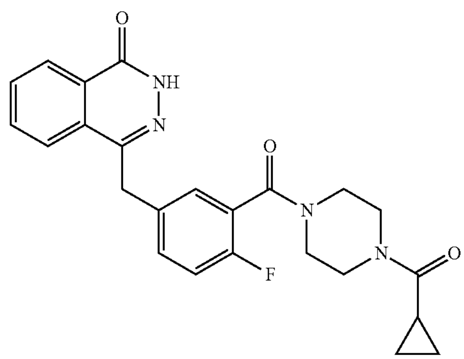

the process comprising:

(a) reacting 2-fluoro-5-formylbenzoic acid, a compound of formula V, with cyclopropyl(piperazin-1-yl) methanone, a compound of formula VI, in the presence of a coupling agent,

V

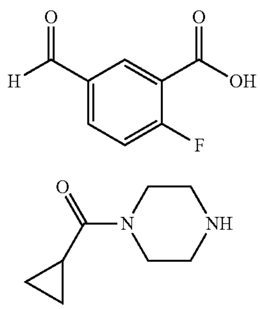

VI to obtain 3-{[4-(cyclopropylcarbonyl) piperazin-1-yl]carbonyl}-4-fluoro benzaldehyde, a compound of formula III,

III

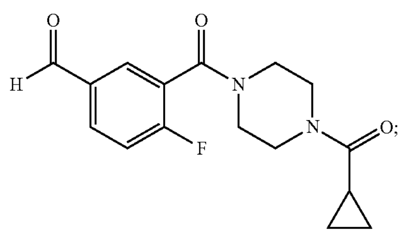

(b) reacting the compound of formula III with dimethyl 3-oxo-1,3-dihydro-2-benzofuran-1-yl) phosphonate, a compound of formula IV,

IV

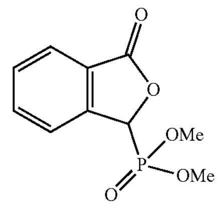

to obtain (3E/Z)-3-({3-[4-(cyclopropanecarbonyl) piperazine-1-carbonyl]-4-fluorophenyl}methylidene)-2-benzofuran-1 (3H)-one, a compound of formula II,

II

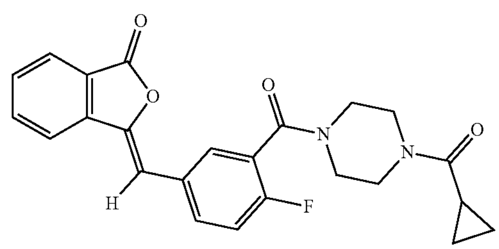

and (c) reacting the compound of formula II with hydrazine hydrate to obtain olaparib, the compound of formula I;

wherein the compound of formula III obtained in step (a) is not isolated, and wherein the coupling agent is selected from the group consisting of EDCI (N-(3-dimethylaminopropyl)-N'-ethylcarbodiimide hydrochloride), DCC (dicyclohexylcarbodiimide), DIC (diisopropylcarbodiimide), HOBt (hydroxybenzotriazole hydrate), HOSu (N-hydroxysuccinimide), HOAt (1-hydroxy-7-azabenzotriazole), DEPBT (3-(diethoxyphosphoryloxy)-1,2,3-benzotriazin-4 (3H)-one), HOOBt (hydroxy-3,4-dihydro-4-oxo-1,2,3-benzotriazine), HDMC (N-[(5-Chloro-3-oxido-1H-benzotriazol-1-yl)-4-morpholinylmethylene]-N-methylmethanaminium hexafluorophosphate), HCTU (2-(6-chloro-1H-benzotriazole-1-yl)-1,1,3,3-tetramethylaminium hexafluorophosphate), HOTT (S-(1-oxido-2-pyridyl)-N,N,N',N'-tetramethylthiuronium hexafluorophosphate), TFFH (tetramethylfluoroformamidinium hexafluorophosphate), TBTU (O-(benzotriazol-1-yl)-N,N,N',N'-tetramethyluronium tetrafluoroborate), TATU (O-(7-azabenzotriazole-1-yl)-1,1,3,3-tetramethyluronium tetrafluoroborate), DMTMM (4-(4,6-dimethoxy-1,3,5-triazin-2-yl)-4-methylmorpholinium tetrafluoroborate), TSTU (N,N,N,N-tetramethyl-O—(N-succinimidyl) uronium tetrafluoroborate), TDBTU (O-(3,4-dihydro-4-oxo-1,2,3-benzotriazin-3-yl)-N,N,N' N'-tetramethyluronium tetrafluoroborate), TPTU (O-(2-oxo-1 (2H) pyridyl)-N,N,N',N'-tetramethyluronium tetrafluoroborate), TOTU (O-[(ethoxycarbonyl)cyanomethylenamino]-N,N,N',N'-tetramethyluronium tetrafluoroborate), TOTT (N,N,N',N'-tetramethyl-S-(1-oxido-2-pyridyl)thiouronium tetrafluoroborate), IIDQ (isobutyl 1,2-dihydro-2-isobutoxy-1-quinolinecarboxylate), EEDQ (N-Ethoxycarbonyl-2-ethoxy-1,2-dihydroquinoline), PyCIU (chlorodipyrrolidinocarbenium hexafluorophosphate), PyOxim ([ethyl cyano(hydroxyimino)acetato-O2]tri-1-pyrrolidinylphosphonium hexafluorophosphate), PyAOP ((7-azabenzotriazol-1-yloxy)tripyrrolidinophosphonium hexafluorophosphate), PyBOP ((benzotriazol-1-yloxy) tripyrrolidinophosphonium hexafluorophosphate), BOP (benzotriazol-1-yloxytris(dimethylamino)phosphonium hexafluorophosphate), COMU ((1-cyano-2-ethoxy-2-oxoethylidenaminooxy)dimethylamino-morpholino-carbenium hexafluorophosphate), Oxyma (ethyl(hydroxyimino) cyanoacetate), FDPP (pentafluorophenyl diphenylphosphinate), and T3P (propylphosphonic anhydride), or a mixture thereof.

2. The process of claim 1, wherein the coupling agent is EDCI (N-(3-dimethylaminopropyl)-N'-ethylcarbodiimide hydrochloride).

3. The process of claim 1, wherein the reaction of the compound of formula V with the compound of formula VI in step (a) occurs in the presence of a base.

4. The process of claim 3, wherein the base is selected from the group consisting of diisopropylethylamine, triethylamine, tributylamine, triphenylamine, pyridine, lutidine, collidine, imidazole, DMAP (4-(dimethylamino)pyridine), DABCO (1,4-diazabicyclo[2.2.2]octane), DBU (1,8-diazabicyclo[5.4.0]undec-7-ene), DBN (1,5-diazabicyclo[4.3.0]non-5-ene), N,N,N',N'-tetramethyl-1,8-naphthalenediamine, N,N,N',N'-tetramethyl-1,8-naphthalenediamine, and HOBt (hydroxybenzotriazole hydrate), or a mixture thereof.

5. The process of claim 1, wherein the reaction of the compound of formula V with the compound of formula VI in step (a) occurs in the presence of a solvent.

6. The process of claim 5, wherein the solvent is selected from the group consisting of halogenated hydrocarbons, ethers, hydrocarbons, esters, nitriles, amides, and sulfoxides, or a mixture thereof.

7. The process of claim 1, wherein the reaction of the compound of formula III with the compound of formula IV in step (b) occurs in the presence of a base.

8. The process of claim 7, wherein the base is selected from the group consisting of diisopropylethylamine, triethylamine, tributylamine, triphenylamine, pyridine, lutidine, collidine, imidazole, DMAP, DABCO, DBU, DBN, N,N,N',N'-tetramethyl-1,8-naphthalenediamine, and lithium hexamethyldisilazide, or a mixture thereof.

9. The process of claim 8, wherein the base is triethylamine or DMAP.

10. The process of claim 1, wherein the reaction of the compound of formula III with the compound of formula IV in step (b) occurs in the presence of a solvent.

11. The process of claim 10, wherein the solvent is selected from the group consisting of ethers, halogenated hydrocarbons, hydrocarbons, esters, nitriles, amides, and sulfoxides, or a mixture thereof.

12. A process for the preparation of crystalline form G1 of olaparib, the process comprising:

a) reacting a solution of a compound of formula II,

II

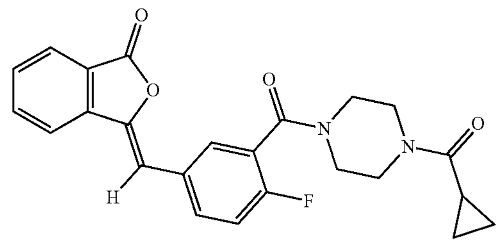

in an amide solvent with hydrazine hydrate at a temperature ranging from about 15° C. to about 35° C. to obtain a reaction mixture;

b) heating the reaction mixture as obtained in step (a) for about 3 hours to about 7 hours at a temperature ranging from about 60° C. to about 80° C. under stirring to obtain olaparib through a compound of formula IIIa:

IIIa

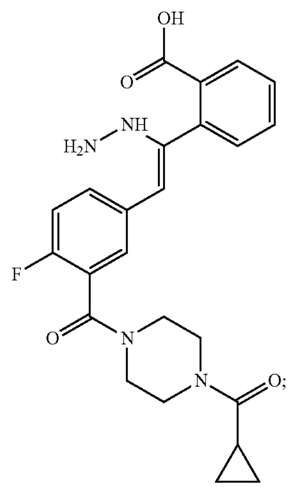

c) adding a haloalkane solvent to a reaction mass as obtained in step (b) to obtain a clear solution, followed by stirring for about 1 hour to 3 hours at a temperature ranging from about 15° C. to about 35° C.;

d) cooling the reaction mass obtained in step (c) to a temperature ranging from about 10° C. to about 0° C. with stirring to obtain crystalline form G1 of olaparib; and e) isolating crystalline Form G1 of olaparib obtained in step (d), wherein the crystalline form G1 of olaparib has an X-ray powder diffraction (XRPD) spectrum having peak reflections at about 15.5, 21.5, 27.4, 30.6 and 38.4±0.2 degrees 2 theta.

13. The process of claim 12, wherein the amide solvent of step (a) is selected from dimethylacetamide or dimethylformamide.

14. The process of claim 12, wherein the crystalline form G1 of olaparib is substantially free of the dimer impurity represented by the following chemical structure.

Dimer

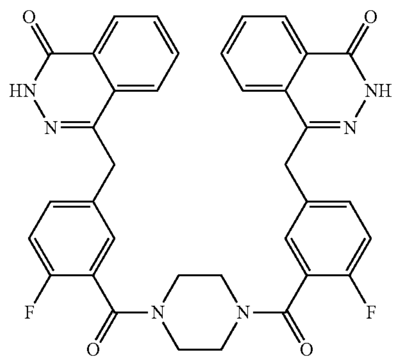

15. The process of claim 12, wherein the process further comprising converting the crystalline form G1 of olaparib to crystalline form H of olaparib by a process comprising the steps of:

(a) providing a solution of crystalline form G1 of olaparib in dimethylsulfoxide; and (b) obtaining crystalline form H of olaparib from the solution of step (a) by combining the solution of step (a) with water; wherein form H has an X-ray powder diffraction pattern containing specific peaks at 6.5, 6.9, 8.4 and 12.8±0.1 degrees 2 theta.

16. A process for the preparation of form H of Olaparib, the process comprising:

(1) reacting a solution of a compound of formula II;

II

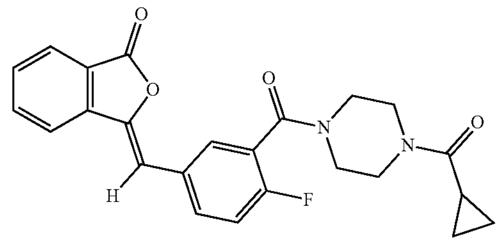

in dimethylsulfoxide with hydrazine hydrate at a temperature ranging from about 20° C. to about 30° C. to obtain a solution;

(2) heating the solution obtained in step (1) for about 5 hours to about 9 hours at a temperature ranging from about 60° C. to about 70° C. under stirring to obtain a reaction mass;

(3) cooling the reaction mass obtained in step (2) to a temperature ranging from about 20° C. to about 30° C., and filtering it to obtain a filtrate;

(4) adding the filtrate obtained in step (3) to water, and stirring the resulting reaction mass; and (5) isolating crystalline Form H of olaparib obtained in step (4).

17. The process of claim 12, further comprising converting the crystalline form G1 of olaparib to crystalline form A of Olaparib by a process comprising:

(a) providing a solution of crystalline form G1 of olaparib in a water-miscible solvent and water;

(b) stirring a reaction mass obtained from the solution of step (a) at a temperature from about 0° C. to about 10° C.;

(c) filtering the reaction mass obtained from the solution of step (b); and (d) obtaining crystalline form A of olaparib from step (c) by combining the filtered reaction mass of step (c) with water.

* * * * *